(12) United States Patent
Bolz et al.

(10) Patent No.: US 11,607,536 B2
(45) Date of Patent: Mar. 21, 2023

(54) ELECTRODE ASSEMBLY FOR NERVE STIMULATION

(71) Applicant: tVNS Technologies GmbH, Erlangen (DE)

(72) Inventors: Lars-Oliver Bolz, Erlangen (DE); Armin Bolz, Erlangen (DE)

(73) Assignee: tVNS Technologies GmbH, Erlangen (DE)

( * ) Notice: Subject to any disclaimer, the term of this patent is extended or adjusted under 35 U.S.C. 154(b) by 0 days.

(21) Appl. No.: 17/082,439

(22) Filed: Oct. 28, 2020

(65) Prior Publication Data

US 2021/0121680 A1 Apr. 29, 2021

(30) Foreign Application Priority Data

Oct. 29, 2019 (DE) ...................... 10 2019 129 098.8

(51) Int. Cl.
*A61N 1/04* (2006.01)
*A61N 1/36* (2006.01)

(52) U.S. Cl.
CPC ........... *A61N 1/0456* (2013.01); *A61N 1/048* (2013.01); *A61N 1/0476* (2013.01); *A61N 1/36014* (2013.01)

(58) Field of Classification Search
CPC ................ A61N 1/456; A61N 1/36036; A61N 1/36014; A61N 1/476; A61N 1/48
See application file for complete search history.

(56) References Cited

U.S. PATENT DOCUMENTS

| | | | |
|---|---|---|---|
| 8,364,274 B1 * | 1/2013 | Litvak | A61N 1/36039 607/57 |
| 2008/0021517 A1 * | 1/2008 | Dietrich | A61N 1/361 607/57 |
| 2008/0249439 A1 | 10/2008 | Tracey et al. | |

FOREIGN PATENT DOCUMENTS

| DE | 102011100065 A1 | 10/2012 |
|---|---|---|
| DE | 102013011541 B3 | 10/2014 |

* cited by examiner

*Primary Examiner* — Alyssa M Alter
(74) *Attorney, Agent, or Firm* — Dilworth & Barrese, LLP

(57) ABSTRACT

The present invention relates to a an electrode assembly for nerve stimulation, in particular for the transcutaneous vagus nerve stimulation, comprising at least one electrode and a bow-shaped holding portion which is designed to hold the electrode assembly at the ear of a patient.

18 Claims, 3 Drawing Sheets

ELECTRODE ASSEMBLY FOR NERVE STIMULATION

BACKGROUND OF THE INVENTION

This present invention relates to an electrode assembly for nerve stimulation according to the description herein.

From the prior art, the so-called transcutaneous vagus nerve stimulation (hereinafter also referred to as t-VNS) is known as a method of treatment, which is based on the fact that a branch of the vagus nerve, namely the Ramus auricularis nervi vagi (RANV), is transcutaneously stimulated with electrical impulses. The method is used for example in the treatment of the drug-resistant epilepsy (DRE) and the refractory depression.

The treatment is carried out with a device that generates electrical impulses which are emitted by an ear electrode, which is worn like an earphone, through the skin to said branch of the vagus nerve.

Conventional ear electrodes have the disadvantage that they are uncomfortable to wear, do not allow the simultaneous use of earphones and also easily fall out of the ear of the patient.

SUMMARY OF THE INVENTION

Thus, it is the object underlying the present invention to attenuate or entirely eliminate the deficiencies known from the prior art.

Concretely, it is the object underlying the present invention to create an electrode assembly for nerve stimulation, which is comfortable to wear, allows a simultaneous use of body earphones and also is safely anchored at the ear of the patient.

This object is achieved by an electrode assembly according to the description herein.

An inventive electrode assembly for nerve stimulation, in particular for the transcutaneous vagus nerve stimulation, includes at least one electrode and a bow-shaped holding portion which is designed to hold the electrode assembly at the ear of a patient.

Preferably, the at least one electrode is connected to the holding portion via a connecting portion, which holding portion a patient can tuck behind his or her ear in the manner of an earpiece in order to anchor the electrode assembly at the ear of the patient.

As the activity of the nerve stimulation largely depends on a good contact between the electrode and the tissue to be stimulated, it has proven to be advantageous in practice when the connecting portion by means of which the electrode is connected to the holding portion is inclined relative to the connecting portion.

In other words, the at least one electrode preferably is connected to the holding portion via a connecting portion, wherein the connecting portion is inclined relative to the holding portion by an angle of preferably between about 5° and about 30°, particularly preferably between about 10° and about 20°, in particular of about 15°.

Due to the inclination of the connecting portion, a safe contact of the electrode with the skin of the patient and a sufficient contact pressure are ensured even during a movement of the patient, for example while sleeping or during sport.

The inclination of the connecting portion relative to the holding portion or of an imaginary straight line perpendicular to the holding portion is such that the electrode is inclined towards the patient proceeding from the holding portion, when the electrode assembly is arranged on/in the ear of the patient.

Furthermore, it has proven to be advantageous in practice when the holding portion and the connecting portion are manufactured from materials of similar hardness, in particular from materials with a Shore hardness in the range of about 30 ShoreD to about 65 ShoreD, preferably in the range of about 40 ShoreD to about 60 ShoreD, particularly preferably in the range of about 45 ShoreD to about 55 ShoreD.

This embodiment is particularly quick and easy to manufacture, as the holding portion and the connecting portion can be manufactured in one common method step, for example by an injection molding method.

Due to the hardness of the materials used, a good structural stability and rigidity of the electrode assembly can also be ensured.

Furthermore, it has proven to be advantageous in practice when at least part of the electrode assembly is manufactured from a relatively soft material.

According to another embodiment, the holding portion and the connecting portion thus are at least partly manufactured from materials of different hardness, in particular from relatively hard materials with a Shore hardness in the range of about 30 ShoreD to about 65 ShoreD, preferably in the range of about 40 ShoreD to about 60 ShoreD, particularly preferably in the range of about 45 ShoreD to about 55 ShoreD and/or from relatively soft materials with a Shore hardness in the range of about 70 ShoreA to about 98 ShoreA, preferably in the range of about 75 ShoreA to about 90 ShoreA, particularly preferably in the range of about 80 ShoreA to about 88 ShoreA.

Due to the mixture/connection of harder materials and softer materials, the advantages of a good structural stability of the electrode assembly as a result of relatively hard materials can be combined with an increased wearing comfort due to relatively soft materials.

Furthermore it has proven to be advantageous in practice when the holding portion largely is manufactured from a relatively hard material and the connecting portion as well as a section of the holding portion preferably directly adjoining the connecting portion are manufactured from materials of different hardness.

Preferably, the part made of relatively hard material is inserted, embedded or sunk in the part made of relatively soft material, or vice versa. This provides for generating a smooth surface, which increases the wearing comfort of the electrode assembly and also has hygienic advantages.

Alternatively, the holding portion also can largely be manufactured from a relatively soft material and the connecting portion as well as a section of the holding portion adjoining the connecting portion can be manufactured from materials of different hardness.

Preferably, the part manufactured from relatively hard material here is also inserted, embedded or sunk in the part manufactured from relatively soft material, or vice versa.

It is also conceivable to merely provide a framework of relatively hard material, which is completely or partly integrated or embedded in a portion made of soft material. For example, the holding portion can include such a framework which is sheathed with a softer material.

Furthermore, it has proven to be advantageous in practice when a cable associated with the at least one electrode extends along the holding portion or within the holding portion and leaves the holding portion at an end of the holding portion opposite to the electrode. Alternatively, the cable can leave the holding portion also at another position.

Preferably, the holding portion includes a guiding groove/receiving groove for guiding/receiving the cable on its outside.

In this way, it can be prevented that the cable reduces the wearing comfort of the electrode assembly.

Furthermore, it has proven to be advantageous when the electrode assembly includes two electrodes. Preferably, the electrodes are made of coated titanium.

Another advantage of the present electrode assembly consists in that the at least one electrode and the bow-shaped holding portion preferably are arranged such that the access to the auditory canal of the patient is not blocked or impeded by the electrode assembly when the electrode assembly is arranged on the ear of the patient.

This is achieved in that the bow-shaped holding portion is tucked behind the ear in the manner of an earpiece, in this position extends around the auricle of the patient at the front in the viewing direction of the patient, and brings the electrode in contact with or presses it against the patient tissue above the auditory canal of the patient.

In other words, the geometry of the electrode assembly is configured such that no components of the electrode assembly are located in front of the auditory canal of the patient when the electrode assembly is arranged on/in the ear of the patient. The electrode rather is held in the auricle of the patient from the front/from above so that the auditory canal remains free.

Another aspect of the invention relates to a device for carrying out a nerve stimulation, in particular a transcutaneous vagus nerve stimulation with at least one electrode assembly according to the invention.

Preferably, the device comprises two electrode assemblies according to the present invention so that a stimulation of the patient is possible in both ears.

BRIEF DESCRIPTION OF THE DRAWINGS

Further advantages, features and effects of the present invention can be taken from the following detailed description of a selected embodiment of the invention with reference to the associated Figures. Similar or identical components in the Figures are designated with the same reference numerals.

IN THE DRAWING

Figure 1:
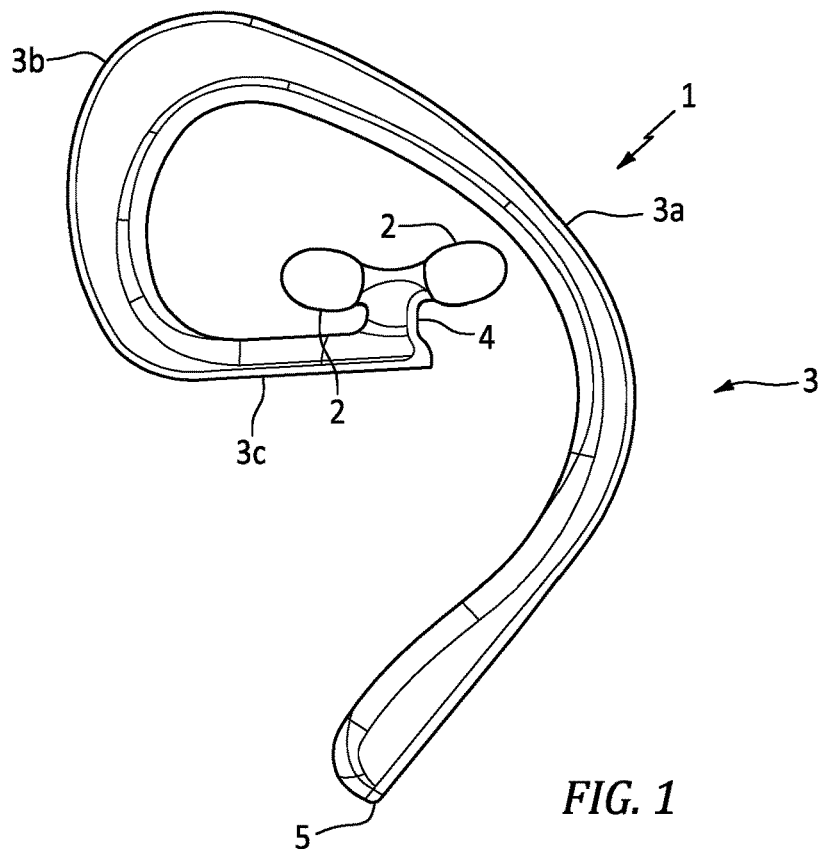

FIG. 1 shows a first embodiment of an electrode assembly according to the invention, in which the holding portion and the connecting portion are manufactured from materials of similar hardness.

Figure 2:
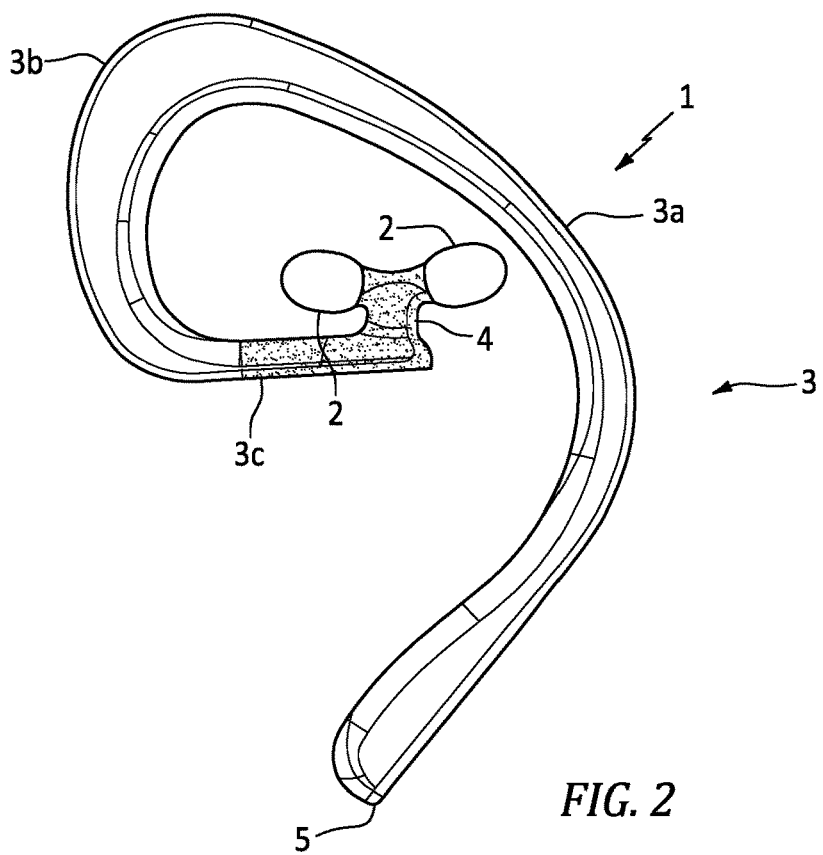

FIG. 2 shows a second embodiment of an electrode assembly according to the invention, in which a large part of the holding portion is manufactured from a relatively hard material, and the connecting portion as well as a section of the holding portion in the vicinity of the connecting portion are manufactured from a mixture of relatively hard and soft materials.

Figure 3:
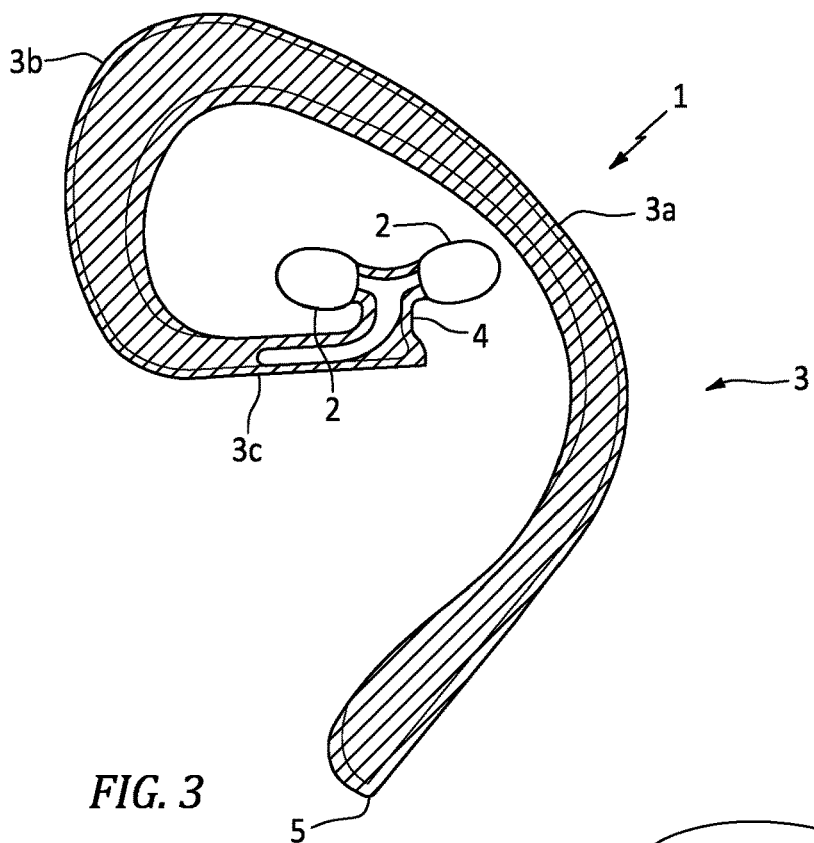

FIG. 3 shows a third embodiment of an electrode assembly according to the invention, in which a large part of the holding portion is manufactured from a relatively soft material, and the connecting portion as well as a section of the holding portion in the vicinity of the connecting portion are manufactured from a mixture of relatively hard and soft materials.

Figure 4:
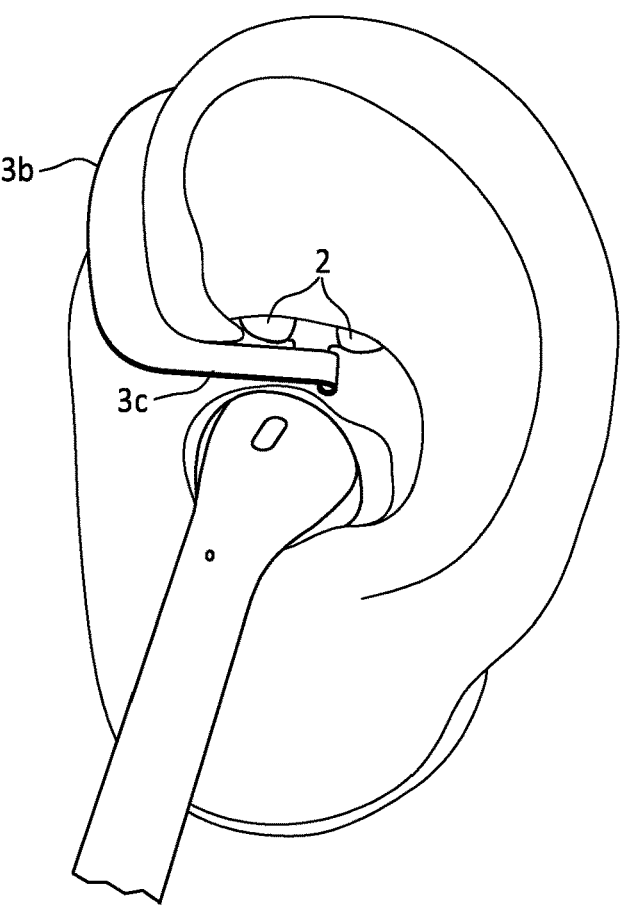

FIG. 4 shows an electrode assembly according to the invention, which is arranged on an ear. As shown in FIG. 4, the simultaneous use of an earphone (in-ear headphone) is easily possible.

Figure 5:
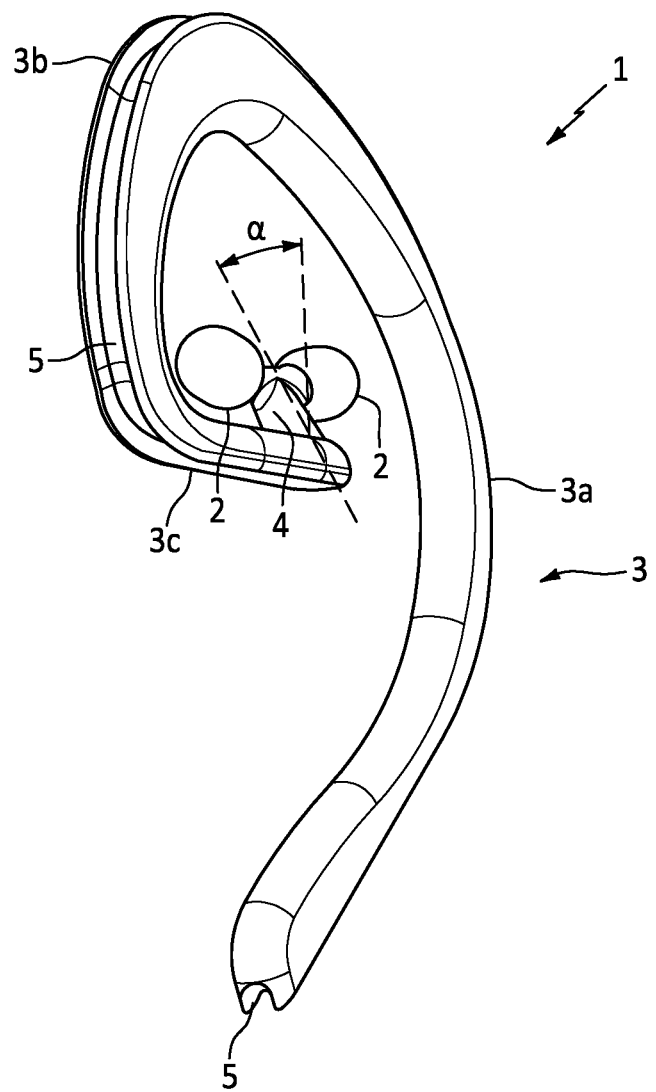

FIG. 5 shows a view of an electrode assembly according to the invention, in which the inclination between the holding portion and the connecting portion is clearly visible.

DESCRIPTION OF THE PREFERRED EMBODIMENTS

As shown in FIG. 1, an electrode assembly 1 according to the invention in one embodiment includes two electrodes 2 and a bow-shaped holding portion 3. The two electrodes are connected to the bow-shaped holding portion 3 via a connecting portion 4.

The bow-shaped holding portion 3 includes a first portion 3a which is of bent design like an earpiece. In addition, the bow-shaped holding portion 3 includes a second portion 3b which directly adjoins the portion 3a and is bent towards the portion 3a.

A third portion 3c of the bow-shaped holding portion 3s extends between the second portion 3b and the connecting portion 4 and is arranged substantially at right angles to the second portion 3b and the connecting portion 4.

A cable associated with the electrode can be arranged in/on the holding portion 3 and leaves the holding portion preferably at its end 5 opposite to the electrodes 2.

The two electrodes 2 extend in a substantially Y-shaped or T-shaped manner away from the connecting portion 4.

As shown in FIG. 2, in a second embodiment of an electrode assembly 1 according to the invention a large part of the holding portion 3 is manufactured from a relatively hard material, and the connecting portion 4 as well as a section or the portion 3c of the holding portion 3 in the vicinity of the connecting portion 4 are manufactured from a mixture of relatively hard and soft materials.

In FIG. 2, the part/area of the portion 3c of the holding portion 3 and the connecting portion 4 are shown hatched.

As shown in FIG. 3, in a third embodiment of an electrode assembly according to the invention a large part of the holding portion 3 is manufactured from a relatively soft material, and the connecting portion 4 as well as a section or the portion 3c of the holding portion 3 are manufactured from a mixture of relatively hard and soft materials.

In FIG. 3, the part/area of the portion 3c of the holding portion 3 and of the connecting portion 4 manufactured from a relatively soft material is shown hatched.

As in this embodiment a large part of the holding portion is made of a relatively soft material, it may be advantageous to provide for the necessary rigidity of the holding portion 3 by means of a framework/inlay made of a relatively hard material inserted in the holding portion 3.

FIG. 4 shows an electrode assembly according to the invention, which is arranged on an ear. As shown in FIG. 4, the simultaneous use of an earphone (in-ear headphone) is easily possible.

As the holding portion 3 extends around the ear of the patient at the top/at the front (at the upper left in FIG. 4) and urges the electrodes 2 in the auricle of the patient against the tissue, the access to the auditory canal of the patient in no way is impeded or blocked by the electrode assembly.

As shown in FIG. 5, the connecting portion 4 preferably is inclined at an angle α relative to the holding portion, in particular to the portion 3c. This provides for a particularly good contact pressure.

Furthermore, FIG. 5 also clearly shows the guiding groove 5 for receiving a cable.

The invention claimed is:

1. An electrode assembly for nerve stimulation, in particular for the transcutaneous vagus nerve stimulation, comprising at least one electrode and a holding portion configured to hold the electrode assembly at an ear of a patient, the electrode being mounted at an inner end of the holding portion, wherein the holding portion comprises three sections, a first outer portion curved or bent in the shape of an earpiece, a second intermediate portion directly adjoining the first portion and bent towards the first portion, and a third inner portion directly adjoining the second portion and extending inwardly from both said first and second portions and back towards said first portion, additionally comprising a connecting portion adjoining an end of said third portion opposite said second portion, and on which said at least one electrode is mounted, wherein the connecting portion is inclined relative to the holding portion at an angle ($\alpha$) between about 5° and about 30°.

2. The electrode assembly according to claim 1, wherein the holding portion and the connecting portion are manufactured from materials of similar hardness.

3. The electrode assembly according to claim 2, wherein the holding portion and the connecting portion are manufactured from materials with a Shore hardness in the range of about 30 ShoreD to about 65 ShoreD.

4. The electrode assembly according to claim 3, wherein the range is from about 40 ShoreD to about 60 ShoreD.

5. The electrode assembly according to claim 4, wherein the range is from about 45 ShoreD to about 55 ShoreD.

6. The electrode assembly according to claim 1, wherein the holding portion and the connecting portion are at least partly manufactured from materials of different hardness.

7. The electrode assembly according to claim 6, wherein the holding portion is largely manufactured from a relatively hard material and the connecting portion as well as a section of the holding portion adjoining the connecting portion are manufactured from materials of different hardness, with a part of the connecting portion and section of the holding portion adjoining the connecting portion manufactured from a relatively hard material being inserted, embedded or sunk in a part of the connecting portion and section of the holding portion adjoining the connecting portion manufactured from a relatively soft material.

8. The electrode assembly according to claim 6, wherein the holding portion is largely manufactured from a relatively soft material and the connecting portion as well as a section of the holding portion adjoining the connecting portion are manufactured from materials of different hardness, with a part of the connecting portion and section of the holding portion adjoining the connecting portion manufactured from a relatively hard material being inserted, embedded or sunk in a part of the connecting portion and section of the holding portion adjoining the connecting portion manufactured from a relatively soft material.

9. The electrode assembly according to claim 6, wherein the holding portion and the connecting portion are at least partly manufactured from at least one of relatively hard materials with a Shore hardness in the range of about 30 ShoreD to about 65 ShoreD, and relatively soft materials with a Shore hardness in the range of about 70 ShoreA to about 98 ShoreA.

10. The electrode assembly according to claim 9, wherein the Shore hardness range for the hard materials is of about 40 ShoreD to about 60 ShoreD, and the Shore hardness in the range for the soft materials is about 75 ShoreA to about 90 ShoreA.

11. The electrode assembly according to claim 10, wherein the Shore hardness range for the hard materials is about 45 ShoreD to about 55 ShoreD, and the Shore hardness in the range for the soft materials is about 80 ShoreA to about 88 ShoreA.

12. The electrode assembly according to claim 1, wherein a cable associated with the at least one electrode extends along the holding portion or within the holding portion and leaves the holding portion at an end of the holding portion opposite to the at least one electrode.

13. The electrode assembly according to claim 1, wherein an additional electrode is provided, with both said electrodes manufactured from coated titanium ($Ti_2$).

14. The electrode assembly according to claim 1, wherein the at least one electrode and the holding portion are arranged such that the access to the auditory canal of the patient is not blocked or impeded by the electrode assembly when the electrode assembly is arranged on the ear of the patient.

15. A device for carrying out a transcutaneous vagus nerve stimulation, comprising at least one electrode assembly according to claim 1.

16. The electrode assembly according to claim 1, wherein the angle ($\alpha$) is between about 10° and about 20°.

17. The electrode assembly according to claim 1, comprising an additional electrode, with both said electrodes extending in a substantially Y-shaped or T-shaped manner away from the connecting portion.

18. The electrode assembly according to claim 1, wherein said third portion is arranged at substantially right angles to the second portion and the connecting portion.

\* \* \* \* \*